(12) United States Patent
Lago et al.

(10) Patent No.: US 7,109,238 B2
(45) Date of Patent: Sep. 19, 2006

(54) CALCILYTIC COMPOUNDS

(75) Inventors: Maria Amparo Lago, Audubon, PA (US); James Francis Callahan, Philadelphia, PA (US); Pradip Kumar Bhatnagar, Exton, PA (US); Eric G. Del Mar, Salt Lake City, UT (US); William M. Bryan, Phoenixville, PA (US); Joelle L. Burgess, Trappe, PA (US)

(73) Assignees: Smith Kline Beecham Corporation, Philadelphia, PA (US); NPS Pharmaceuticals, Inc., Salt Lake City, UT (US)

( * ) Notice: Subject to any disclaimer, the term of this patent is extended or adjusted under 35 U.S.C. 154(b) by 303 days.

(21) Appl. No.: 10/761,986

(22) Filed: Jan. 21, 2004

(65) Prior Publication Data
US 2004/0192741 A1 Sep. 30, 2004

Related U.S. Application Data

(63) Continuation of application No. 10/181,338, filed as application No. PCT/US01/02402 on Jan. 24, 2001, now abandoned.

(60) Provisional application No. 60/177,683, filed on Jan. 24, 2000.

(51) Int. Cl.
*A61K 31/335* (2006.01)
*A61K 31/195* (2006.01)
*C07C 303/08* (2006.01)
*C07C 63/04* (2006.01)
*C07D 255/03* (2006.01)

(52) U.S. Cl. .................. 514/475; 514/567; 514/520; 514/521; 549/551; 558/414; 560/51; 562/493

(58) Field of Classification Search ............... 558/414; 560/51; 549/551; 562/493; 514/475, 567, 514/520, 521
See application file for complete search history.

(56) References Cited

U.S. PATENT DOCUMENTS

| 4,645,678 A | 2/1987 | Nofre et al. | |
|---|---|---|---|
| 6,022,894 A * | 2/2000 | Del Mar et al. | ............. 514/524 |
| 6,395,919 B1 * | 5/2002 | Bhatnagar et al. | .......... 558/414 |

FOREIGN PATENT DOCUMENTS

| WO | WO97/37967 | 10/1997 |
|---|---|---|
| WO | WO98/45255 | 10/1998 |
| WO | 66/51569 | * 10/1999 |
| WO | WO99/51241 | 10/1999 |
| WO | WO99/51569 | 10/1999 |
| WO | WO01/08673 | 2/2001 |

OTHER PUBLICATIONS

Mangnus, E. M. et al., Journal of Agricultural and Food Chemistry, vol. 40 No. 7, 1222-1227, (1992).

* cited by examiner

*Primary Examiner*—Johann Richter
*Assistant Examiner*—Ebenezer Sackey
(74) *Attorney, Agent, or Firm*—Soma G. Simon; Mary McCarthy; Charles Kinzig

(57) ABSTRACT

Novel calcilytic compounds and methods of using them are provided.

6 Claims, No Drawings

CALCILYTIC COMPOUNDS

This is a continuation of application Ser. No. 10/181,338, filed 17 Jul. 2002, now abandoned which is a 35 USC 371 of application PCT/US01/02402 filed 24 Jan. 2001. Benefit is claimed under Title 35 USC 119(e) of Application No. 60/177,683 filed 24 Jan. 2000.

FIELD OF INVENTION

The present invention relates to novel calcilytic compounds, pharmaceutical compositions containing these compounds and their use as calcium receptor antagonists.

In mammals, extracellular $Ca^{2+}$ is under rigid homeostatic control and regulates various processes such as blood clotting, nerve and muscle excitability, and proper bone formation. Extracellular $Ca^{2+}$ inhibits the secretion of parathyroid hormone ("PTH") from parathyroid cells, inhibits bone resorption by osteoclasts, and stimulates secretion of calcitonin from C-cells. Calcium receptor proteins enable certain specialized cells to respond to changes in extracellular $Ca^{2+}$ concentration.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. See Brown et al., Nature 366:574, 1993. In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, reviewed in Nemeth et al., Cell Calcium 11:319, 1990. For example, extracellular $Ca^{2+}$ plays a role in parafollicular (C-cells) and parathyroid cells. See Nemeth, Cell Calcium 11:323, 1990. The role of extracellular $Ca^{2+}$ on bone osteoclasts has also been studied. See Zaidi, Bioscience Reports 10:493, 1990.

Various compounds are known to mimic the effects of extra-cellular $Ca^{2+}$ on a calcium receptor molecule. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators, which are active at $Ca^{2+}$ receptors. Such calcilytics are useful in the treatment of various disease states characterized by abnormal levels of one or more components, e.g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

SUMMARY OF THE INVENTION

The present invention comprises novel calcium receptor antagonists represented by Formula (I) hereinbelow and their use as calcium receptor antagonists in the treatment of a variety of diseases associated with abnormal bone or mineral homeostasis, including but not limited to hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

The present invention further provides a method for antagonizing calcium receptors in an animal, including humans, which comprises administering to an animal in need thereof an effective amount of a compound of Formula (I), indicated hereinbelow.

The present invention further provides a method for increasing serum parathyroid levels in an animal, including humans, which comprises administering to an animal in need thereof an effective amount of a compound of Formula (I), indicated herein below.

DETAILED DESCRIPTION OF THE INVENTION

The compounds of the present invention are selected from Formula (I) herein below:

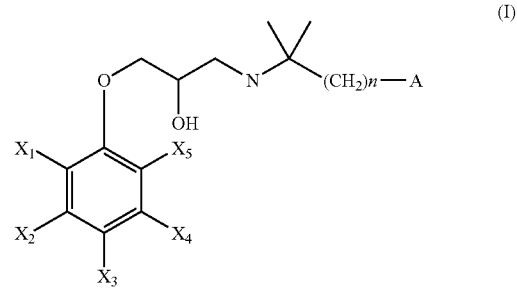

wherein:

A is an aryl or fused aryl, dihydro or tetrahydro fused aryl, heteroaryl or fused heteroaryl, dihydro or tetrahydro fused heteroaryl, unsubstituted or substituted with any substituent being selected from the group consisting of OH, halogen, $C_{1-4}$alkyl, $C_{1-4}$alkoxy, $C_{3-6}$ cycloalkyl, $CF_3$, $OCF_3$, CN, and $NO_2$;

$X_1$ and $X_5$ are independently selected from the group consisting of H, halogen, CN, and $NO_2$, provided that either $X_1$ or $X_5$ is H;

$X_2$, $X_3$ and $X_4$ are selected from the group consisting of H, halogen, O—$C_{1-4}$alkyl, and J-K, wherein:

J is a covalent bond, alkylene, O-alkylene or alkenylene; and
K is selected from the group consisting of, $CO_2R_5$, $CONR_4R'_4$, OH, $NR_4R'_4$ and CN;
$R_4$ and $R'_4$ are independently H, alkyl, aryl or heteroaryl;
$R_5$ is H, alkyl, alkyl-(O-alkyl)$_m$-O-alkyl; n is an integer from 0 to 4; and
m is an integer from 1–3.

Preferred compounds of the present invention have a structure according to Formula (II) hereinbelow:

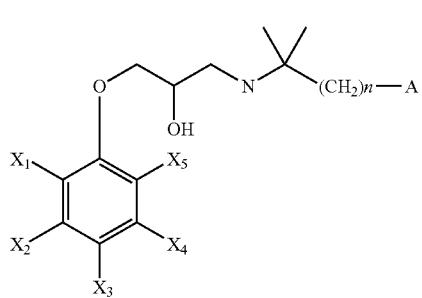

(II)

wherein:
A is an aryl or fused aryl, dihydro or tetrahydro fused aryl, heteroaryl or fused heteroaryl, dihydro or tetrahydro fused heteroaryl, unsubstituted or substituted with any substituent being selected from the group consisting of halogen, $C_{1-4}$alkyl, $C_{1-4}$alkoxy, $CF_3$, and $OCF_3$;
$X_1$ and $X_5$ are independently selected from the group consisting of H, halogen, CN, and $NO_2$, provided that either $X_1$ or $X_5$ is H;
$X_2$, $X_3$ and $X_4$ are selected from the group consisting of H, halogen, O—$C_{1-4}$ alkyl, and J-K, wherein:
J is a covalent bond, alkylene, O-alkylene or alkenylene;
K is selected from the group consisting of, $CO_2R_5$, $CONR_4R'_4$, and $NR_4R'_4$;
$R_4$ and $R'_4$ are independently H, alkyl, aryl or heteroaryl;
$R_5$ is H, alkyl, or alkyl-(O-alkyl)$_m$-O-alkyl;
n is an integer from 0 to 4; and
m is an integer from 1–3.

More preferred compounds of the present invention have a structure according to Formula (III) hereinbelow:

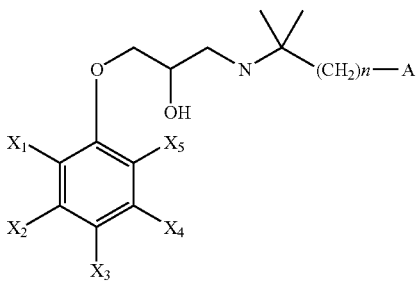

(III)

wherein:
A is an aryl or fused aryl, dihydro or tetrahydro fused aryl, heteroaryl or fused heteroaryl, dihydro or tetrahydro fused heteroaryl, unsubstituted or substituted with any substituent being selected from the group consisting of halogen, $C_{1-4}$alkoxy, $CF_3$, and $OCF_3$;
$X_1$ and $X_5$ are independently selected from the group consisting of H, halogen and CN, provided that either $X_1$ or $X_5$ is H;
$X_2$, $X_3$ and $X_4$ are selected from the group consisting of H, halogen, O—$C_{1-4}$ alkyl, and J-K, wherein:
J is a covalent bond, alkylene, O-alkylene or alkenylene; and
K is $CO_2R_5$;
$R_5$ is H, or alkyl; and
n is an integer from 0 to 4.

As used herein, "alkyl" refers to an optionally substituted hydrocarbon group joined by single carbon-carbon bonds and having 1–20 carbon atoms joined together. The alkyl hydrocarbon group may be linear, branched or cyclic, saturated or unsaturated. Preferably, substituents on optionally substituted alkyl are selected from the group consisting of aryl, heteroaryl, $CO_2R_1$, $CO_2NR_1R_1'$, OH, $OR_1$, $COR_1$, $NR_1R_1'$, halogen, $CF_3$, $OCF_3$ and $NO_2$, wherein $R_1$ represents H, $C_{1-4}$ alkyl, $C_{3-6}$ cycloalkyl, $C_{2-5}$ alkenyl, $C_{2-5}$ alkynyl, heterocycloakyl, aryl or heteroaryl, $C_{1-4}$ alkyl; additional substituents are selected from F, Cl, Br, I, N, S and O. Preferably, no more than three substituents are present. More preferably, the alkyl has 1–12 carbon atoms and is unsubstituted. Preferably, the alkyl group is linear.

As used herein "cycloalkyl" refers to optionally substituted 3–7 membered carbocyclic rings wherein any substituents are selected from the group consisting of, F, Cl, Br, I, $N(R_1)_2$, $SR_1$ and $OR_1$, unless otherwise indicated.

As used herein "alkylene" is a linker of up to 5 carbon atoms, unsubstituted or substituted by a substituent selected from the group consisting of $C_{1-4}$ alkyl, $NR_4R'_4$, OH, O (forming a ketone), aryl, heteroaryl.

As used herein "alkenylene" is a linker of up to 5 carbon atoms containing one unsaturation, unsubstituted or substituted by a substituent selected from the group consisting of $C_{1-4}$ alkyl, $NR_4R'_4$, OH, O (forming a ketone), aryl, heteroaryl.

As used herein, "aryl" refers to an optionally substituted aromatic group with at least one ring having a conjugated pi-electron system, containing up to two conjugated or fused ring systems. Aryl includes carbocyclic aryl, and biaryl groups, all of which may be optionally substituted. Preferred aryl include phenyl and naphthyl. More preferred aryl include phenyl. Preferred substituents are selected from the group consisting of halogen, $C_{1-4}$ alkyl, $OCF_3$, $CF_3$, OMe, CN, $OSO_2R_2$ and $NO_2$, wherein $R_2$ represents $C_{1-4}$ alkyl or $C_{3-6}$ cycloalkyl.

As used herein, "heteroaryl" refers to an optionally substituted aromatic group with at least one ring having a conjugated pi-electron system, containing up to two conjugated or fused ring systems and 1–3 heteroatoms selected from O, S and N. Heteroaryl includes carbocyclic heteroarylaryl, aryl-heteroaryl aid biheteroarylaryl groups, all of which may be optionally substituted. Preferred aryl include phenyl and naphthyl. More preferred aryl include phenyl. Preferred substituents are selected from the group consisting of halogen, $C_{1-4}$ alkyl, $OCF_3$, $CF_3$, OMe, CN, $OSO_2R_2$ and $NO_2$, wherein $R_2$ represents $C_{1-4}$ alkyl or $C_{3-6}$ cycloalkyl.

As used herein, "alkenyl" refers to an optionally substituted hydrocarbon group containing at least one carbon-carbon double bond and containing up to 5 carbon atoms joined together. The alkenyl hydrocarbon chain may be straight, branched or cyclic. Any substituents are selected from the group consisting of halogen, $C_{1-4}$ alkyl, $OCF_3$, $CF_3$, OMe, CN, $OSO_2R_3$ and $NO_2$, wherein $R_3$ represents $C_{1-4}$ alkyl or $C_{3-6}$ cycloalkyl.

As used herein, "alkynyl" refers to an optionally substituted hydrocarbon group containing at least one carbon-carbon triple bond between the carbon atoms and containing up to 5 carbon atoms joined together. The alkynyl hydrocarbon group may be straight-chained, branched or cyclic. Any substituents are selected from the group consisting of halogen, $C_{1-4}$ alkyl, $OCF_3$, $CF_3$, OMe, CN, $OSO_2R_3$ and $NO_2$, wherein $R_3$ represents $C_{1-4}$ alkyl or $C_{3-6}$ cycloalkyl.

The compounds of the present invention may contain one or more asymmetric carbon atoms and may exist in racemic and optically active forms. All of these compounds and diastereomers are contemplated to be within the scope of the present invention.

Preferred compounds of the present inventions include:

3-{4-Cyano-3-[(R)-2-hydroxy-3-(2-indan-2-yl-1,1-dimethyl-ethylamino)-propoxy]-phenyl}-propionic ethyl ester;

3-{4-Cyano-3-[(R)-2-hydroxy-3-(2-indan-2-yl-1,1-dimethyl-ethylamino)-propoxy]-phenyl}-propionic acid;

3-{4-Cyano-3-[(S)-2-hydroxy-3-(2-indan-2-yl-1,1-dimethyl-ethylamino)-propoxy]-phenyl}-propionic ethyl ester;

3-{4-Cyano-3-[(S)-2-hydroxy-3-(2-indan-2-yl-1,1-dimethyl-ethylamino)-propoxy]-phenyl}-propionic acid;

3-{4-Cyano-3-[(R)-2-hydroxy-3-(2-indan-2-yl-1,1-dimethyl-ethylamino)-propoxy]-phenyl}-propionic acid octyl ester;

3-{4-Cyano-3-[(R)-2-hydroxy-3-(2-indan-2-yl-1,1-dimethyl-ethylamino)-propoxy]-phenyl}-propionic acid 2-methoxy-ethyl ester;

3-{4-Cyano-3-[(R)-2-hydroxy-3-(2-indan-2-yl-1,1-dimethyl-ethylamino)-propoxy]-phenyl}-propionic acid butyl ester;

3-{4-Cyano-3-[(R)-2-hydroxy-3-(2-indan-2-yl-1,1-dimethyl-ethylamino)-propoxy]-phenyl}-propionic acid isopropyl ester;

3-{4-Cyano-3-[(R)-2-hydroxy-3-(2-indan-2-yl-1,1-dimethyl-ethylamino)-propoxy]-phenyl}-propionic acid pentyl ester;

3-{4-Cyano-3-[(R)-2-hydroxy-3-(2-indan-2-yl-1,1-dimethyl-ethylamino)-propoxy]-phenyl}-propionic acid 2-ethoxy ethyl ester;

3-{4-cyano-3-[(R)-2-hydroxy-3-(2-indan-2-yl-dimethyl-ethylamino)-propoxy]-phenyl}-propionic acid 3-methyl-butyl ester;

3-{4-cyano-3-[(R)-2-hydroxy-3-(2-indan-2-yl-dimethyl-ethylamino)-propoxy]-phenyl}-propionic acid 1-ethyl-propyl ester;

3-{4-cyano-3-[(R)-2-hydroxy-3-(2-indan-2-yl-dimethyl-ethylamino)-propoxy]-phenyl}-propionic acid sec-butyl ester;

3-{4-cyano-3-[(R)-2-hydroxy-3-(2-indan-2-yl-dimethyl-ethylamino)-propoxy]-phenyl}-propionic acid 2-methoxy-1-methyl-ethyl ester;

2,2-Dimethyl-propionic acid 3-{4-cyano-3-[(R)-2-hydroxy-3-(2-indan-2-yl-1,1-dimethyl-ethylamino)-propoxy]-phenyl}-propanoyloxymethyl ester;

3-{4-Cyano-3-[(R)-2-hydroxy-3-(2-indan-2-yl-1,1-dimethyl-ethylamino)-propoxy]-phenyl}-propionic acid (S)-2-amino-3-methyl-butyl ester;

3-{4-Cyano-3-[(R)-2-hydroxy-3-(2-indan-2-yl-1,1-dimethyl-ethylamino)-propoxy]-phenyl}-propionic acid 5-amino-pentyl ester;

3-{4-Cyano-3-[(R)-2-hydroxy-3-(2-indan-2-yl-1,1-dimethyl-ethylamino)-propoxy]-phenyl}-propionic acid methyl ester;

3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid 3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid ethyl ester;

3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid;

3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid ethyl ester;

3-{4-Cyano-3-[(R)-2-hydroxy-3-(2-indan-5-yl-1,1-dimethyl-ethylamino)-propoxy]-phenyl}-propionic acid;

3-{4-Cyano-3-[(R)-2-hydroxy-3-(2-indan-5-yl-1,1-dimethyl-ethylamino)-propoxy]-phenyl}-propionate ethyl ester;

3-{2-Chloro-4-cyano-5-[(R)-2-hydroxy-3-(2-indan-2-yl-1,1-dimethyl-ethylamino)-propoxy]-phenyl}-propionic ethyl ester;

3-{2-Chloro-4-cyano-5-[(R)-2-hydroxy-3-(2-indan-2-yl-1,1-dimethyl-ethylamino)-propoxy]-phenyl}-propionic acid;

3-{2-Fluoro-4-cyano-5-[(R)-2-hydroxy-3-(2-indan-2-yl-1,1-dimethyl-ethylamino)-propoxy]-phenyl}-propionic ethyl ester;

3-{2-Fluoro-4-cyano-5-[(R)-2-hydroxy-3-(2-indan-2-yl-1,1-dimethyl-ethylamino)-propoxy]-phenyl}-propionic acid;

3-{2-Cyano-3-[(R)-3-(1,1-dimethyl-2-naphthalen-2-yl-ethylamino)-2-hydroxy-propoxy]-phenyl}-propionic acid ethyl ester;

4-{2-Cyano-3-[(R)-3-(1,1-dimethyl-2-naphthalen-2-yl-ethylamino)-2-hydroxy-propoxy]-phenyl}-butyric acid ethyl ester;

3-{2-Cyano-3-[(R)-3-(1,1-dimethyl-2-naphthalen-2-yl-ethylamino)-2-hydroxy-propoxy]-phenyl}-propionic acid;

4-{2-Cyano-3-[(R)-3-(1,1-dimethyl-2-naphthalen-2-yl-ethylamino)-2-hydroxy-propoxy]-phenyl}-butyric acid;

4-{4-Cyano-3-[(R)-3-(1,1-dimethyl-2-naphthalen-2-yl-ethylamino)-2-hydroxy-propoxy]-phenyl}-butyric acid ethyl ester;

4-{4-Cyano-3-[(R)-3-(1,1-dimethyl-2-naphthalen-2-yl-ethylamino)-2-hydroxy-propoxy]-phenyl}-butyric acid;

4-{3-Cyano-4-[(R)-3-(1,1-dimethyl-2-naphthalen-2-yl-ethylamino)-2-hydroxy-propoxy]-phenyl}-butyric acid ethyl ester;

4-{3-Cyano-4-[(R)-3-(1,1-dimethyl-2-naphthalen-2-yl-ethylamino)-2-hydroxy-propoxy]-phenyl}-butyric acid;

3-{2-Cyano-3-[(R)-3-(2-indan-2-yl-1,1-dimethyl-ethylamino)-2-hydroxy-propoxy]-phenyl}-propionic acid ethyl ester;

4-{2-Cyano-3-[(R)-3-(2-indan-2-yl-1,1-dimethyl-ethylamino)-2-hydroxy-propoxy]-phenyl}-butyric acid ethyl ester;

3-{2-Cyano-3-[(R)-3-(2-indan-2-yl-1,1-dimethyl-ethylamino)-2-hydroxy-propoxy]-phenyl}-propionic acid;

4-{2-Cyano-3-[(R)-3-(2-indan-2-yl-1,1-dimethyl-ethylamino)-2-hydroxy-propoxy]-phenyl}-butyric acid;

4-{4-Cyano-3-[(R)-3-(2-indan-2-yl-1,1-dimethyl-ethylamino)-2-hydroxy-propoxy]-phenyl}-butyric acid ethyl ester;

4-{4-Cyano-3-[(R)-3-(2-indan-2-yl-1,1-dimethyl-ethylamino)-2-hydroxy-propoxy]-phenyl}-butyric acid;

4-{3-Cyano-4-[(R)-3-(2-indan-2-yl-1,1-dimethyl-ethylamino)-2-hydroxy-propoxy]-phenyl}-butyric acid ethyl ester;

4-{3-Cyano-4-[(R)-3-(2-indan-2-yl-1,1-dimethyl-ethylamino)-2-hydroxy-propoxy]-phenyl}-butyric acid;

(S)-2-Amino-3-{4-[(R)-3-(1,1-dimethyl-2-naphthalen-2-yl-ethylamino)-2-hydroxy-propoxy]-3-nitro-phenyl}-propionic acid ethyl ester;

(S)-2-Amino-3-{4-[(R)-3-(1,1-dimethyl-2-naphthalen-2-yl-ethylamino)-2-hydroxy-propoxy]-3-nitro-phenyl}-propionic acid;

(R)-2-Amino-5-{4-cyano-3-[(R)-2-hydroxy-3-(2-indan-2-yl-1,1-dimethyl-ethylamino)-propoxy]-phenyl}-pentanoic acid ethyl ester;

(R)-2-Amino-5-{4-cyano-3-[(R)-2-hydroxy-3-(2-indan-2-yl-1,1-dimethyl-ethylamino)-propoxy]-phenyl}-pentanoic acid;

5-{4-Cyano-3-[(R)-2-hydroxy-3-(2-indan-2-yl-1,1-dimethyl-ethylamino)-propoxy]-phenyl}-pentanoic acid ethyl ester;

5-{4-Cyano-3-[(R)-2-hydroxy-3-(2-indan-2-yl-1,1-dimethyl-ethylamino)-propoxy]-phenyl}-pentanoic acid;

(R)-2-Amino-5-{4-cyano-3-[(R)-2-hydroxy-3-(2-indan-2-yl-1,1-dimethyl-ethylamino)-propoxy]-phenyl}-propionic acid ethyl ester;

(R)-2-Amino-5-{4-cyano-3-[(R)-2-hydroxy-3-(2-indan-2-yl-1,1-dimethyl-ethylamino)-propoxy]-phenyl}-propionic acid;

(S)-2-Amino-5-{4-cyano-3-[(R)-2-hydroxy-3-(2-indan-2-yl-1,1-dimethyl-ethylamino)-propoxy]-phenyl}-propionic acid ethyl ester; and (S)-2-Amino-5-{4-cyano-3-[(R)-2-hydroxy-3-(2-indan-2-yl-1,1-dimethyl-ethylamino)-propoxy]-phenyl}-propionic acid;

and pharmaceutically acceptable salts thereof.

More preferred compounds of the present invention include:

3-{4-Cyano-3-[(R)-2-hydroxy-3-(2-indan-2-yl-1,1-dimethyl-ethylamino)-propoxy]-phenyl}-propionic ethyl ester;

3-{4-Cyano-3-[(R)-2-hydroxy-3-(2-indan-2-yl-1,1-dimethyl-ethylamino)-propoxy]-phenyl}-propionic acid;

3-{4-Cyano-3-[(R)-2-hydroxy-3-(2-indan-2-yl-1,1-dimethyl-ethylamino)-propoxyl]-phenyl}-propionic acid isopropyl ester;

3-{4-Cyano-3-[(R)-2-hydroxy-3-(2-indan-2-yl-1,1-dimethyl-ethylamino)-propoxy]-phenyl}-propionic acid 2-ethoxy ethyl ester;

3-{4-cyano-3-[(R)-2-hydroxy-3-(2-indan-2-yl-dimethyl-ethylamino)-propoxy]-phenyl}-propionic acid 2-methoxy-1-methyl-ethyl ester;

3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid 3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid ethyl ester;

3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid;

3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid ethyl ester;

3-{4-Cyano-3-[(R)-2-hydroxy-3-(2-indan-5-yl-1,1-dimethyl-ethylamino)-propoxy]-phenyl)-propionic acid; and 3-{4-Cyano-3-[(R)-2-hydroxy-3-(2-indan-5-yl-1,1-dimethyl-ethylamino)-propoxy]-phenyl}-propionate ethyl ester and pharmaceutically acceptable salts and complexes thereof.

Most preferred compounds of the present invention include:

3-{4-Cyano-3-[(R)-2-hydroxy-3-(2-indan-2-yl-1,1-dimethyl-ethylamino)-propoxy]-phenyl}-propionic ethyl ester; and 3-{4-Cyano-3-[(R)-2-hydroxy-3-(2-indan-2-yl-1,1-dimethyl-ethylamino)-propoxy]-phenyl}-propionic acid;

and pharmaceutically acceptable salts and complexes thereof.

Pharmaceutically acceptable salts are non-toxic salts in the amounts and concentrations at which they are administered.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. A preferred salt is a hydrochloride. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present invention provides compounds of Formula (I) above, which can be prepared using standard techniques. An overall strategy for preparing preferred compounds described herein can be carried out as described in this section. The examples that follow illustrate the synthesis of specific compounds. Using the protocols described herein as a model, one of ordinary skill in the art can readily produce other compounds of the present invention.

All reagents and solvents were obtained from commercial vendors. Starting materials (e.g., amines and epoxides) were synthesized using standard techniques and procedures.

Compounds of Formula (I) are prepared by the general methods described in Schemes 1–3. In general, a solution of a glycidyl ether (e.g., 7 of Scheme 1) and a primary amine (e.g., 2-indan-2-yl-1,1-dimethyl-ethylamine of Scheme 1) in a solvent such as absolute ethanol, acetonitrile, toluene, THF or any other similar solvent optionally in the presence of a suitable catalyst such as $LiClO_4$ (0.1–2 equiv.) is stirred overnight or longer at reflux. The product (e.g., 8-Scheme 1) is purified by chromatography and/or recrystallization. An acid salt e.g., hydrochloride salt is prepared by treatment of the corresponding free base with the acid (e.g., HCl either in gas phase or 4M dioxane solution), or by any other standard method. Hydrolysis of the ester under either basic or acidic conditions yields the corresponding acid (e.g., 9-Scheme 1).

A general synthesis of the epoxide with compound 7 as an example is outlined in Scheme 2.

The syntheses of some of the required amines are outlined in Scheme 3.
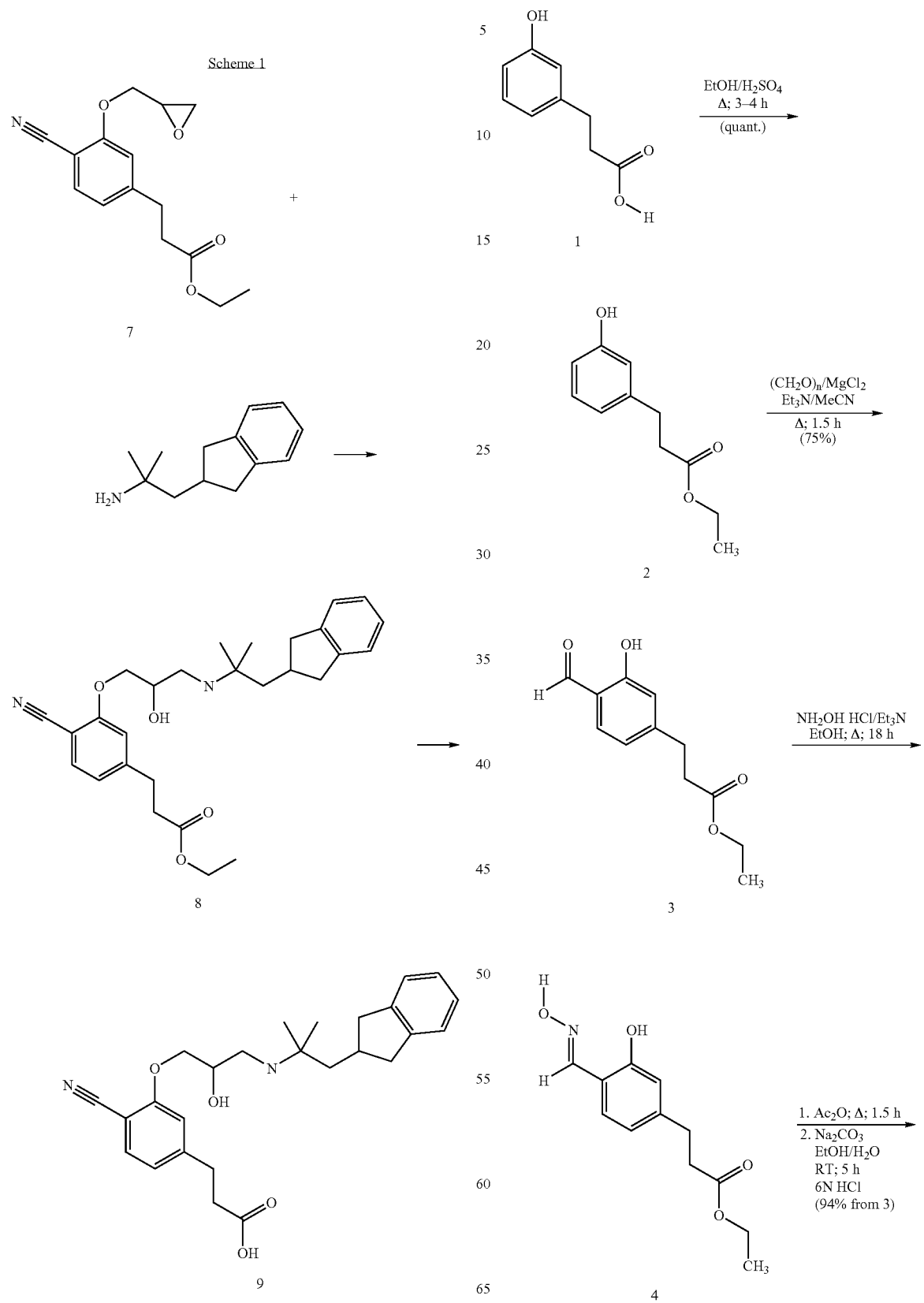

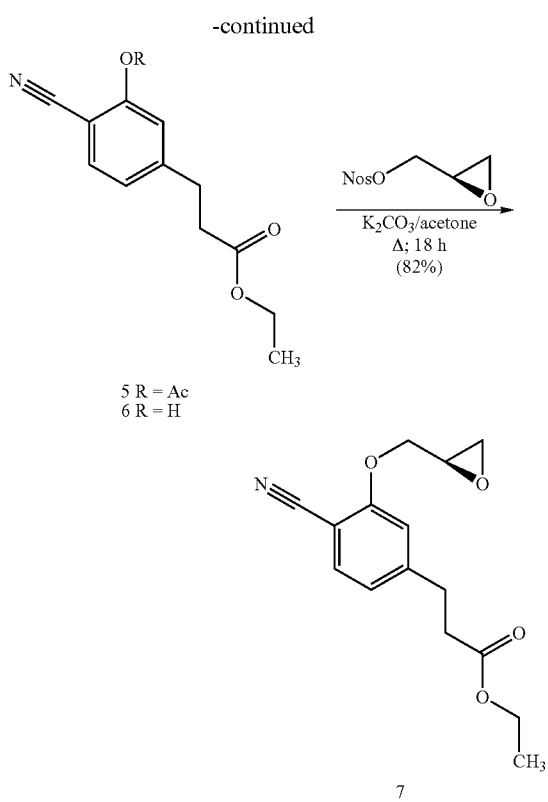

Scheme 3

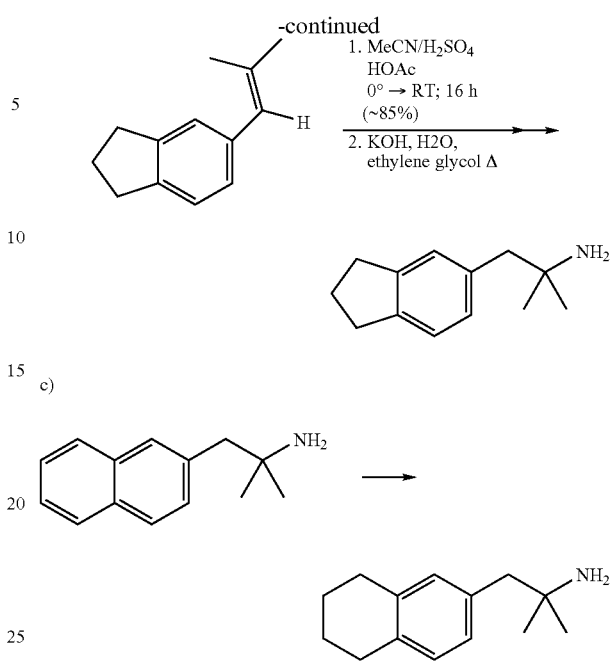

In order to use a compound of Formula (I) or a pharmaceutically acceptable salt thereof for the treatment of humans and other mammals, it is normally formulated in accordance with standard pharmaceutical practice as a pharmaceutical composition.

The calcilytic compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art. The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably, the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered, for example, from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

Diseases and disorders which might be treated or prevented, based upon the affected cells, include bone and mineral-related diseases or disorders; hypoparathyroidism; those of the central nervous system such as seizures, stroke, head trauma, spinal cord injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney, such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon; GI ulcer diseases; GI diseases with excessive calcium absorption such as sarcoidosis; autoimmune diseases and organ transplant rejection; squamous cell carcinoma; and pancreatitis.

In a preferred embodiment of the present invention, the present compounds are used to increase serum parathyroid hormone ("PTH") levels. Increasing serum PTH levels can be helpful in treating diseases such as hypoparathyroidism, osteosarcoma, periodontal disease, fracture, osteoarthritis, rheumatoid arthritis, Paget's disease, humoral hypercalcemia malignancy and osteoporosis.

Another aspect of the present invention describes a method of treating a patient comprising administering to the patient an amount of a present compound sufficient to increase the serum PTH level. Preferably, the method is carried out by administering an amount of the compound effective to cause an increase in duration and/or quantity of serum PTH level sufficient to have a therapeutic effect.

In various embodiments, the compound administered to a patient causes an increase in serum PTH having a duration of up to one hour, about one to about twenty-four hours, about one to about twelve hours, about one to about six hours, about one to about five hours, about one to about four hours, about two to about five hours, about two to about four hours, or about three to about six hours.

In an alternative embodiment of the present invention, the compound administered to a patient causes an increase in serum PTH having a duration of more than about twenty-four hours provided that it is co-administered with an anti resorptive agent.

In additional different embodiments, the compound administered to a patient causes an increase in serum PTH of up to two fold, two to five fold, five to ten fold, and at least 10 fold, greater than peak serum PTH in the patient. The peak serum level is measured with respect to a patient not undergoing treatment.

In a preferred embodiment of the present invention, the present compound is co-administered with an anti-resorptive agent. Suitable anti-resorptive agents for co-administration include, but are not limited to estrogen, 1, 25 $(OH)_2$ vitamin D3, calcitonin, selective estrogen receptor modulators, vitronectin receptor antagonists, V-H+-ATPase inhibitors, src $SH_2$ antagonists, bisphosphonates and cathepsin K inhibitors.

Composition of Formula (I) and their pharmaceutically acceptable salts, which are active when given orally, can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the following tests:

(I) Calcium Receptor Inhibitor Assay

Calcilytic activity was measured by determining the $IC_{50}$ of the test compound for blocking increases of intracellular $Ca^{2+}$ elicited by extracellular $Ca^{2+}$ in HEK 293 4.0–7 cells stably expressing the human calcium receptor. HEK 293 4.0–7 cells were constructed as described by Rogers et al., *J. Bone Miner. Res.* 10 Suppl. 1:S483, 1995 (hereby incorporated by reference herein). Intracellular $Ca^{2+}$ increases were elicited by increasing extracellular $Ca^{2+}$ from 1 to 1.75 mM. Intracellular $Ca^{2+}$ was measured using fluo-3, a fluorescent calcium indicator.

The procedure was as follows:

1. Cells were maintained in T-150 flasks in selection media (DMEM supplemented with 10% fetal bovine serum and 200 ug/mL hygromycin B), under 5% $CO_2$:95% air at 37° C. and were grown up to 90% confluency.

2. The medium was decanted and the cell monolayer was washed twice with phosphate-buffered saline (PBS) kept at 37° C. After the second wash, 6 mL of 0.0$_2$% EDTA in PBS was added and incubated for 4 minutes at 37° C. Following the incubation, cells were dispersed by gentle agitation.

3. Cells from 2 or 3 flasks were pooled and pelleted (100×g). The cellular pellet was resuspended in 10–15 mL of SPF-PCB+ and pelleted again by centrifugation. This washing was done twice.

Sulfate- and phosphate-free parathyroid cell buffer (SPF-PCB) contains 20 mM Na-Hepes, pH 7.4, 126 mM NaCl, 5 mM KCl, and 1 mM $MgCl_2$. SPF-PCB was made up and stored at 4° C. On the day of use, SPF-PCB was supplemented with 1 mg/mL of D-glucose and 1 mM $CaCl_2$ and then split into two fractions. To one fraction, bovine serum albumin (BSA; fraction V, ICN) was added at 5 mg/mL (SPF-PCB+). This buffer was used for washing, loading and maintaining the cells. The BSA-free fraction was used for diluting the cells in the cuvette for measurements of fluorescence.

4. The pellet was resuspended in 10 mL of SPF-PCB+ containing 2.2 uM fluo-3 (Molecular Probes) and incubated at room temperature for 35 minutes.

5. Following the incubation period, the cells were pelleted by centrifugation. The resulting pellet was washed with SPF-PCB+. After this washing, cells were resuspended in SPF-PCB+ at a density of 1–2×106 cells/mL.

6. For recording fluorescent signals, 300 uL of cell suspension were diluted in 1.2 mL of SPF buffer containing 1 mM $CaCl_2$ and 1 mg/mL of D-glucose. Measurements of fluorescence were performed at 37° C. with constant stirring using a spectrofluorimeter. Excitation and emission wavelengths were measured at 485 and 535 nm, respectively. To calibrate fluorescence signals, digitonin (5 mg/mL in ethanol) was added to obtain Fmax, and the apparent Fmin was determined by adding Tris-EGTA (2.5 M Tris-Base, 0.3 M EGTA). The concentration of intracellular calcium was calculated using the following equation:

Intracellular calcium=$(F-F_{min}/F_{max}) \times K_d$; where $K_d$=400 nM.

7. To determine the potential calcilytic activity of test compounds, cells were incubated with test compound (or vehicle as a control) for 90 seconds before increasing the concentration of extracellular $Ca^{2+}$ from 1 to 2 mM. Calcilytic compounds were detected by their ability to block, in a concentration-dependent manner, increases in the concentration of intracellular $Ca^{2+}$ elicited by extracellular $Ca^{2+}$.

In general, those compounds having lower $IC_{50}$ values in the Calcium Receptor Inhibitor Assay are more preferred compounds. Compounds having an $IC_{50}$ greater than 50 uM were considered to be inactive. Preferred compounds are those having an $IC_{50}$ of 10 uM or lower, more preferred compounds have an $IC_{50}$ of 1 uM, and most preferred compounds have an $IC_{50}$ of 0.1 uM or lower.

(II) Calcium Receptor Binding Assay

HEK 293 4.0–7 cells stably transfected with the Human Parathyroid Calcium Receptor ("HuPCaR") were scaled up in T180 tissue culture flasks. Plasma membrane is obtained by polytron homogenization or glass douncing in buffer (50 mM Tris-HCl pH 7.4, 1 mM EDTA, 3 mM $MgCl_2$) in the presence of a protease inhibitor cocktail containing 1 uM Leupeptin, 0.04 uM Pepstatin, and 1 mM PMSF. Aliquoted membrane was snap frozen and stored at −80° C. $^3$H labeled compound was radiolabeled to a radiospecific activity of 44 Ci/mmole and was aliquoted and stored in liquid nitrogen for radiochemical stability.

A typical reaction mixture contains 2 nM $^3$H compound ((R,R)-N-4'-Methoxy-t-3-3'-methyl-1'-ethylphenyl-1-(1-naphthyl)ethylamine), or $^3$H compound (R)-N-[2-Hydroxy-3-(3-chloro-2-cyanophenoxy)propyl]-1,1-dimethyl-2-(4-methoxyphenyl)ethylamine 4–10 ug membrane in homogenization buffer containing 0.1% gelatin and 10% EtOH in a reaction volume of 0.5 mL. Incubation is performed in 12×75 polyethylene tubes in an ice water bath. To each tube 25 uL of test sample in 100% EtOH is added, followed by 400 uL of cold incubation buffer, and 25 uL of 40 nM $^3$H-compound in 100% EtOH for a final concentration of 2 nM. The binding reaction is initiated by the addition of 50 uL of 80–200 ug/mL HEK 293 4.0–7 membrane diluted in incubation buffer, and allowed to incubate at 4° C. for 30 min. Wash buffer is 50 mM Tris-HCl containing 0.1% PEI. Nonspecific binding is determined by the addition of 100-fold excess of unlabeled homologous ligand, and is generally 20% of total binding. The binding reaction is terminated by rapid filtration onto 1% PEI pretreated GF/C filters using a Brandel Harvestor. Filters are placed in scintillation fluid and radioactivity assessed by liquid scintillation counting.

EXAMPLES

Nuclear magnetic resonance spectra were recorded at either 300 or 400 MHz using, respectively, a Bruker ARX 300 or Bruker AVANCE 400 spectrometer. $CDCl_3$ is deuteriochloroform,-DMSO-$d_6$ is hexadeuteriodimethylsulfoxide, and $CD_3OD$ is tetradeuteriomethanol. Chemical shifts are reported in parts per million (Δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Fourier transform infrared (FTIR) spectra were recorded on a Nicolet 510 infrared spectrometer. FTIR spectra were recorded in transmission mode, and band positions are reported in inverse wavenumbers ($cm^{-1}$). Mass spectra were taken on either a SCIEX5 or Micromass instruments, using electrospray (ES) ionization techniques. Elemental analyses were obtained using a Perkin-Elmer 240C elemental analyzer. Melting

Example 1

Preparation of 2-Indan-2-yl-1,1-dimethyl-ethylamine a) Indan-2-yl-acetic acid methyl ester A solution of indan-2-yl-acetic acid (Lancaster, 20 g, 0.11 mol) in methanol (200 mL) was stirred and cooled to 0–10° C. in an ice bath and treated drop-wise with thionyl chloride (14.8 g, 0.125 mol). The mixture was stirred at RT for 16 h, concentrated in vacuo, and the oily residue was dissolved in ethyl acetate, washed with 2.5 N sodium hydroxide, water, and brine, dried ($MgSO_4$), and concentrated in vacuo to give the title compound (21 g, 97%) which solidified.

b) 1-Indan-2-yl-2-methyl-propan-2-ol

A solution of the compound from Example 1(a) (6.3 g, 33 mmol) in ether (150 mL) was added drop-wise to 1.4 M methyllithium in ether (100 mL, 4.25 eq) stirred in an ice bath. The mixture was allowed to warm to RT, stirred for 2 h, and very carefully quenched by drop-wise addition of saturated aqueous ammonium chloride (150 mL). The aqueous phase was separated and extracted with ether, and the combined ether phase was washed with brine, dried ($MgSO_4$), and concentrated in vacuo to afford the title compound as an oil which crystallized on standing (~89%).

c) N-(2-Indan-2-yl-1,1-dimethyl-ethyl)-acetamide

To a mixture of concentrated sulfuric acid (1.7 mL) in acetonitrile (6 mL) stirred in an ice bath for 45 min. a drop-wise solution of the compound from Example 1(b) (3.3 g, 17.3 mmol) in glacial acetic acid (5 mL) was added. The mixture was allowed to warm to RT, stirred for 16 h, poured into ice water, and extracted with ethyl acetate. The combined organic extract was washed with 2.5 N sodium hydroxide, water, and brine, dried ($MgSO_4$), and concentrated in vacuo to give an oily residue that was triturated with hexane and a few drops of ethyl acetate, seeded, and cooled to afford a solid which was isolated by filtration to afford the title compound as tan solid (1.9 g, 47%). MS(ES) m/e 231.9 $[M+H]^+$. The filtrate was concentrated in vacuo to afford additional title compound as an oil (1.5 g, 37%).

d) 2-Indan-2-yl-1,1-dimethyl-ethylamine

A mixture of the compound from Example 1(c) (6.5 g, 28 mmol) in ethylene glycol (170 mL) was treated with crushed potassium hydroxide pellets (13 g), stirred, and heated to 190° C. for 24 h. The mixture was poured into water and extracted with ethyl acetate. The combined organic phase was washed with brine and extracted with 1 N hydrochloric acid. The combined acidic extract was washed with ethyl acetate, basified with 2.5 N sodium hydroxide, and extracted with ethyl acetate. The combined organic extract was washed with brine, dried ($MgSO_4$), and concentrated in vacuo to afford the title compound (3.2 g, 60%). MS(ES) m/e 190.6 $[M+H]^+$.

Example 2

Preparation of ethyl (R)-4-cyano-3-(oxiranylmethoxy)benzenepropionate a) Ethyl 3-hydroxybenzenepropionate A solution of 3-(3-hydroxyphenyl)propionic acid (Lancaster, 66.4 g, 0.4 mol) in ethanol (700 mL) was treated with concentrated sulfuric acid (6 mL), heated to reflux for 2 h, and allowed to cool to RT. The mixture was cooled in ice, neutralized with 10% aqueous sodium carbonate and concentrated in vacuo to about 50 mL. Water (~200 mL) was added and the mixture was extracted three-times with ethyl acetate. The combined ethyl acetate extract was washed with water and brine, dried ($Na_2SO_4$), filtered, and concentrated in vacuo to yield the title compound as an oil (70 g, 90%).

b) Ethyl 4-formyl-3-hydroxybenzenepropionate

To a solution of the compound from Example 2(a) (77.2 g, 0.4 mol) in dry acetonitrile (1 L) stirred under argon was added triethylamine (152 g, 1.5 mol) followed by magnesium chloride (57.1 g, 0.6 mol). After stirring for 5 min, paraformaldehyde (81 g) was added and the reaction was refluxed under argon for 1.5 h. The reaction was cooled, 6 N hydrochloric acid (400 mL) was added and the resulting mixture was extracted with ethyl acetate. The combined ethyl acetate extract was washed with water, dried ($MgSO_4$), filtered and concentrated in vacuo. The residual oil was purified by flash column chromatography (silica gel, 10% ethyl acetate/hexane) to give the title compound (66.6 g, 75%).

c) Ethyl 3-hydroxy-4-[(hydroxyimino)methyl]benzenepropionate

A solution of the compound from Example 2(b) (66.6 g, 0.3 mol) in absolute ethanol (500 mL) was treated with triethylamine (40.4 g, 0.4 mol) followed by hydroxylamine hydrochloride (23 g, 0.33 mol). The reaction was stirred under argon at reflux for 18 h, concentrated in vacuo, and the residual oil was dissolved in ethyl acetate and washed with 1N hydrochloric acid. The ethyl acetate phase was dried ($MgSO_4$), filtered, and concentrated in vacuo to give the title compound as an oil which was used in the next step.

d) Ethyl 3-acetoxy-4-cyanobenzenepropionate

The compound from Example 2(c) was treated with acetic anhydride (500 mL) and refluxed under argon for 90 min. The reaction was concentrated in vacuo and the resulting oil was dissolved in ethyl acetate and washed with water. The ethyl acetate layer was dried ($MgSO_4$), filtered, and concentrated in vacuo to give the title compound as an oil which was used in the next step.

e) Ethyl 4-cyano-3-hydroxybenzenepropionate

A solution of the compound from Example 2(d) was dissolved in ethanol (200 mL) and treated with a solution of sodium carbonate (64 g, 0.6 mol) in water (1.5 L). After stirring at RT for 5 h, the mixture was neutralized with 6 N hydrochloric acid to pH 5 and concentrated in vacuo. The resulting mixture was extracted with ethyl acetate. The ethyl acetate solution was dried ($MgSO_4$), filtered, and concentrated in vacuo to give the title compound as an oil [61.9 g, 94.2% overall yield from the compound of Preparation 2(c)].

f) Ethyl (R)-4-cyano-3-(oxiranylmethoxy)benzenepropionate

A solution of the compound from Example 2(e) (28.3 g, 0.13 mol) and (2R)-glycidyl 3-nitrobenzenesulfonate (33.7 g, 0.13 mol) in dry acetone (500 mL) was treated with potassium carbonate (36 g, 0.26 mol) and refluxed under argon for 18 h. The reaction was cooled, filtered, and the filtrate was concentrated in vacuo and the residue was purified by flash column chromatography (silica, 30% ethyl acetate/hexane) to yield the title compound (29.5 g, 82.4%).

Example 3

Preparation of Ethyl 3-{4-Cyano-3-[(R)-2-hydroxy-3-(2-indan-2-yl-1,1-dimethyl-ethylamino)-propoxy]-phenyl}-propionate A mixture the compounds from Example 2(f) (6 g, 31.7 mmol) and Example 1(d) (8.6 g, 31.7 mmol) in absolute ethanol (200 mL) was stirred and heated to reflux for 56 h, cooled, concentrated in vacuo. The residue was dissolved in dichloromethane (30 mL) and acidified with 1.0 N hydrogen chloride in ether. The white solid which formed was isolated by filtration and recrystallized to afford the title compound (10 g, 63%). mp (dichloromethane/ether) 155–157° C.; MS(ES) m/e 465.4 [M+H]+.

Example 4

Preparation of 3-{4-Cyano-3-[(R)-2-hydroxy-3-(2-indan-2-yl-1,1-dimethyl-ethylamino)-propoxy]-phenyl}-propionic acid A solution of the compound from Example 3 (1.5 g, 3 mmol) in ethanol (120 mL) and water (40 mL) was treated with 2.5 N sodium hydroxide (5 mL) and stirred for RT under argon overnight. The ethanol was removed in vacuo, and the pH was adjusted to pH 5 with 1 N hydrochloric acid while stirring. The precipitated white solid was collected by filtration, washed with water and dried in vacuo to afford the title compound (1.3 g, quant). MS(ES) m/e 437.4 [M+H]+.

Example 5

Preparation of 3-{4-Cyano-3-[(R)-2-hydroxy-3-(2-indan-2-yl-1,1-dimethyl-ethylamino)-propoxy]-phenyl}-propionic acid hydrochloride The compound from Example 4 (80 mg, 0.18 mmol) was suspended in acetonitrile (8 mL) and treated with 1 N hydrogen chloride in ether dropwise with stirring until the solid dissolved. The mixture was quickly filtered and cooled in an ice bath. The white crystalline solid which formed was isolated by filtration, washed with ether, and dried in vacuo to afford the title compound (80 mg, 94%). Mp 180–181° C.; MS(ES) m/e 437.2 [M+H]+.

Example 6

Preparation of 3-{4-Cyano-3-[(R)-2-hydroxy-3-(2-indan-2-yl-1,1-dimethyl-ethylamino)-propoxy]-phenyl}-propionic acid octyl ester hyrochloride salt A solution of the compound from Example 5 (100 mg, 0.2 mmol) in dry DMF (15 mL) was treated with cesium carbonate (141 mg, 0.4 mmol) and 18-crown-6 (100 mg, 0.41 mmol) followed by 1-iodooctane (144 mg, 0.6 mmol). The resulting mixture was heated at 70° C. under argon for 20 h. The reaction was cooled, concentrated and the residue partitioned between water and ethyl acetate. The organic layer was washed with 10% $Na_2CO_3$ (aqueous), brine, dried over $MgSO_4$ and evaporated. Purification by flash chromatography (4% MeOH in $CH_2Cl_2$) gave the ester as a yellow oil. The oil in ether was treated with HCl and filtered to give the above titled compound (50 mg, 46%). LC-MS m/e 549.4 [M+H]+.

Example 7

Preparation of 3-{4-Cyano-3-[(R)-2-hydroxy-3-(2-indan-2-yl-1,1-dimethyl-ethylamino)-propoxy]-phenyl}-propionic acid 2-methoxy-ethyl ester hyrochloride salt Using the procedure of Example 6 but substituting 1-bromo-2-methoxy-ethane for 1-iodooctane gave the above titled compound. LC-MS m/e 495.4 [M+H]+.

Example 8

Preparation of 3-{4-Cyano-3-[(R)-2-hydroxy-3-(2-indan-2-yl-1,1-dimethyl-ethylamino)-propoxy]-phenyl}-propionic acid butyl ester hyrochloride salt Using the procedure of Example 6 but substituting 1-iodobutane for 1-iodooctane gave the above titled compound. LC-MS m/e 493.4 [M+H]+.

Example 9

Preparation of 3-{4-Cyano-3-[(R)-2-hydroxy-3-(2-indan-2-yl-1,1-dimethyl-ethylamino)-propoxyl-phenyl}-propionic acid isopropyl ester trifluoroacetate salt a) 3-(4-Cyano-3-hydroxy-phenyl)-propionic acid A solution of 3-(4-Cyano-3-hydroxy-phenyl)-propionic acid ethyl ester (2.2 g, 10 mmol) in ethanol (10 mL) and water (40 mL) was treated with aqueous sodium hydroxide solution (2.5 M, 44 mL) at room temperature overnight. The solvent was removed under vacuum and the residue was dissolved in water (150 mL). The pH of the aqueous solution was adjusted to 2–4 by the addition of 3N HCl (aqueous) and the precipitate was then filtered and washed with water to give the title compound as white solid (1.88 g, 0.98 mmol, 98.4% yield). ESMS m/z: 192 [M+H]+.

b) 3-(4-cyano-3-hydroxy-phenyl)-propionic acid isopropyl ester

A solution of compound from Example 9(a) (0.25 g, 1.3 mmol) and propan 2-ol (0.4 g, 0.67 mmol) in $CH_2Cl_2$ (10 ml) was treated dropwise with a solution of 4-pyrrolidinopyridine (0.2 g, 1.3 mmol) in $CH_2Cl_2$ (1 mL). The reaction mixture under $N_2$ was cooled to 0° C. and then treated with EDC (1-[3-(dimethylamino) propyl]-3-ethylcarbodiimide hydrochloride (Aldirch, 0.27 g, 1.4 mmol). The subsequent mixture was stirred at 0° C. for 30 min and slowly brought to room temperature and stirred overnight. The reaction mixture was washed with 3 N HCl (3×25 mL), brine (1×25 mL) and H$_2$O (1×25 mL). The organic layer was dried over anhydrous sodium sulfate and concentrated under vacuum to give the above titled compound.

c) 3-(4-Cyano-3-oxiranylmethoxy-phenyl)-propionic acid isopropyl ester

A solution of compound from Example 9(b), R-glycidyl-nosylate (0.33 g, 1.4 mmol) and K$_2$CO$_3$ (0.36 g, 2.6 mmol) in acetone (10 mL) was refluxed under N$_2$ overnight. The reaction mixture was then cooled to room temperature and filtered. The filtrate was concentrated under vacuum to give the above titled compound as a light brown oil.

d) 3-{4-Cyano-3-[(R)-2-hydroxy-3-(2-indan-2-yl-1,1-dimethyl-ethylamino)-propoxyl]-phenyl}-propionic acid isopropyl ester trifluoroacetate salt The compound from Example 9(c) and the compound from Example 1(d) was dissolved in toluene (12.5 mL) and the mixture was stirred at 120° C. overnight. The solvent was removed under vacuum and the residue was purified by preparative HPLC (Gilson) to give the above titled compound as a light yellow oil. ESMS m/z: 479 [M+H]$^+$.

Example 10

Preparation of 3-{4-Cyano-3-[(R)-2-hydroxy-3-(2-indan-2-yl-1,1-dimethyl-ethylamino)-propoxy]-phenyl}-propionic acid pentyl ester trifluoroacetate salt The title compound was prepared by the same procedure as Example 9 except that propan-2-ol was replaced with pentan-1-ol to give the above titled compound as oil. ESMS m/z: 507 [M+H]$^+$.

Example 11

Preparation of 3-{4-Cyano-3-[(R)-2-hydroxy-3-(2-indan-2-yl-1,1-dimethyl-ethylamino)-propoxy]-phenyl}-propionic acid 2-ethoxy ethyl ester trifluoroacetate salt The title compound was prepared by the same procedure as Example 9 except that propan-2-ol was replaced with 2-ethoxy-ethanol to give the above titled compound as an oil. ESMS m/z: 509 [M+H]$^+$.

Example 12

Preparation of 3-{4-Cyano-3-[(R)-2-hydroxy-3-(2-indan-2-yl-1,1-dimethyl-ethylamino)-propoxy]-phenyl}-propionic acid 2-methoxy ethyl ester trifluoroacetate salt The title compound was prepared by the same procedure as Example 9 except that propan-2-ol was replaced with 2-methoxy-ethanol to give the above titled compound as an oil. ESMS m/z: 495 [M+H]$^+$.

Example 13

Preparation of 3-{4-cyano-3-[(R)-2-hydroxy-3-(2-indan-2-yl-dimethyl-ethylamino)-propoxy]-phenyl}-propionic acid methyl-butyl ester trifluoroacetate salt The title compound was prepared by the same procedure as Example 9 except that propan-2-ol was replaced with 3-methyl-butan-1-ol to give the above titled compound as an oil. ESMS m/z: 507 [M+H]$^+$.

Example 14

Preparation of 3-{4-cyano-3-[(R)-2-hydroxy-3-(2-indan-2-yl-dimethyl-ethylamino)-propoxy]-phenyl}-propionic acid 1-ethyl-propyl ester trifluoroacetate salt The title compound was prepared by the same procedure as Example 9 except that propan-2-ol was replaced with pentan-3-ol to give the above titled compound as an oil. ESMS m/z: 507 [M+H]$^+$.

Example 15

Preparation of 3-{4-cyano-3-[(R)-2-hydroxy-3-(2-indan-2-yl-dimethyl-ethylamino)-propoxy]--phenyl}-propionic acid sec-butyl ester trifluoroacetate salt The title compound was prepared by the same procedure as Example 9 except that propan-2-ol was replaced with butan-2-ol to give the above titled compound as an oil. ESMS m/z: 493 [M+H]$^+$.

Example 16

Preparation of 3-(4-cyano-3-[(R)-2-hydroxy-3-(2-indan-2-yl-dimethyl-ethylamino)-propoxy]-phenyl}-propionic acid 2-methoxy-1-methyl-ethyl ester The title compound was prepared by the same procedure as Example 9 except that propan-2-ol was replaced with 1-methoxy-propan-2-ol to give the above titled compound as an oil. ESMS m/z: 509 [M+H]$^+$.

Example 17

Preparation of 2,2-Dimethyl-propionic acid 3-{4-cyano-3-1(R)-2-hydroxy-3-(2-indan-2-yl-1,1-dimethyl-ethylamino)-pro poxy]-phenyl}-propanoyloxymethyl ester hydrochloride salt To a suspension of 200 mg (0.44 mmole) of the sodium salt of the compound from Example 4 in 10 mL of DMF was added 17 mg (0.011 mmole) of sodium iodide, 290 mg (1.1 mmole) of 18-crown-6 and 100 g (0.66 mmole) of chloromethylpivalate. The reaction was stirred at 70° C. for 24 h and concentrated to a gum which was purified by flash chromatography on silica gel eluting with 4% MeOH in CH$_2$Cl$_2$ to yield 100 mg of an oil which was treated with 1N HCl/ether to yield the above titled compound (90 mg) as a white solid. ES-MS m/z: 551 [M+H]$^+$.

Example 18

Preparation of 3-{4-Cyano-3-[(R)-2-hydroxy-3-(2-indan-2-yl-1,1-dimethyl-ethylamino)-propoxy]-phenyl}-propionic acid (S)-2-amino-3-methyl-butyl ester a) 3-(4-Cyano-3-hydroxy-phenyl)-propionic acid (S)-2-tert-butoxycarbonylamino-3-methyl-butyl ester To 0.95 g (5 mmol) of 4-cyano-3-hydroxybenzenepropionic acid, 0.74 g (5 mmol) of 4-pyrrolinopyridine, 1.06 g (5.5 mmol) of EDC.HCl in 25 mL of THF was added 1.02 g (4.5 mmol) of t-butyloxycarbonyl-S-valinol. The reaction was stirred 18 h. The reaction was concentrated, diluted with EtOAc and washed with 3N HCl and 5% $NaCO_3$. The EtOAc extracts were concentrated and the residue was purified by flash chromatography on silica gel eluting with 10% EtOH in $CH_2Cl_2$ to yield 1.73 g of the above titled compound as a yellow oil ESMS m/z: 377 $[M+H]^+$.

b) 3-[14-Cyano-3-((R)-1-oxiranylmethoxy)-phenyl]-propionic acid (S)-2-tert-butoxycarbonylamino-3-methyl-butyl ester.

To 1.73 gm (0.0046 mole) of the compound from Example 18 (a) in 25 mL of acetone was added 1.19 g (4.6 mmol) of (2R)-glycidyl 3-nitrobenzenesulfonate and 1.38 g (10 mmol) of $K_2CO_3$. The mixture was heated at reflux for 18 h, filtered and concentrated to give the above titled compound as a gum which was used without purification.

c) 3-{4-Cyano-3-[(R)-2-hydroxy-3-(2-indan-2-yl-1,1-dimethyl-ethylamino)-propoxy]-phenyl}-propionic acid (S)-2-amino-3-methyl-butyl ester To 0.43 g (1 mmol) of the compound from Example 18 (b) in 25 mL of MeCN was added 0.19 g (1 mmol) of 2-indan-2-yl-1,1-dimethyl-ethylamine and the reaction heated at reflux for 18 h. The mixture was concentrated and treated for 30 min with 10 mL of a solution of 1:1 $TFA-CH_2Cl_2$. The reaction was concentrated and the resulting oil was purified by preparative HPLC on a 50×20 mm ID YMC Combiprep ODS column eluting at 20 mL/min with a linear gradient of 30% MeCN(0.1% TFA)/30% water(0.1% TFA) to 70% MeCN(0.1% TFA) over 15 min to give the above titled compound (25 mg). ESMS m/z: 522 $[M+H]^+$.

Example 19

Preparation of 3-{4-Cyano-3-[(R)-2-hydroxy-3-(2-indan-2-yl-1,1-dimethyl-ethylamino)-propoxy]-phenyl}-propionic acid 5-amino-pentyl ester The title compound was prepared by the same procedure as Example 18 except that t-butyloxycarbonylpentanol was used in place of t-butyloxycarbonyl-S-valinol to give the above titled compound (22 mg). ESMS m/z: 522 $[M+H]^+$.

Example 20

Preparation of 3-{4Cyano-3-[(R)-2-hydroxy-3-(2-indan-2-yl-1,1-dimethyl-ethylamino)-propoxy]-phenyl}-propionic acid methyl ester hydrochloride To 100 mg of the compound from Example 3 in 100 mL of methanol was added 1 mL of 12M HCl. The reaction was heated at reflux for 72 h and then concentrated to yield the above titled compound (77 mg) as a white powder. ESMS m/z: 451 $[M+H]^+$.

Example 21

Preparation of 3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid a) 6-(1,1-Dimethyl-1-aminoethyl)-1,2,3,4-tetrahydronaphthalene hydrochloride A solution of 1.0 g (4.2 mmol) of 6-(1,1-dimethyl-1-aminoethyl)naphthalene hydrochloride in glacial acetic acid (100 mL) was treated under Argon atmosphere with $PtO_2$ (350 mg). The mixture was hydrogenated in a Parr shaker at 50 psi for 1 h. and filtered through a plug of celite. The filtrate was concentrated in vacuo and concentrated from ether. The residue was triturated with ether and the white crystalline solid (850 mg, 85% yield) was collected, washed with ether and dried. MS(ES) m/z 204.2$(M+H)^+$; Elemental analysis: theoretical for $C_{14}H_{21}N.HCl.1/2 H_2O$: C, 67.58; H, 9.31; N, 5.63. found: C, 67.51; H, 9.31; N, 5.63.

b) 3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid ethyl ester.

Following the procedure described in Example 3 except using amine from Example 21(a), the above titled compound was obtained. MS(ES) m/z 479.6 $(M+H)^+$; Elemental analysis: theoretical for $C_{29}H_{38}N_2O_4.HCl.1/2H_2O$: C, 66.46; H, 7.60; N, 5.34; found: C, 66.11; H, 7.66; N, 5.24.

c) 3-(4-Cyano-3-{(R)-3-[1,1-dimethyl-2-(5,6,7,8tetrahydro-naphthalen-2-yl)-ethylamino]-2-hydroxy-propoxy}-phenyl)-propionic acid.

Following the procedure described in Experiment 4 for the ester hydrolysis of compound in experiment 21(b) the above titled compound was obtained. MS(ES) m/z 451.7 $(M+H)^+$.

Example 22

Preparation of 3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid Following the procedure described in Example 3 using ethyl (R)-2-cyano-4-(oxiranylmethoxy)benzenepropionate and the amine from example 21(a) the above titled compound was obtained. MS(ES) m/z 451.4 $(M+H)^+$.

Example 23

3-{4-Cyano-3-[(R)-2-hydroxy-3-(2-indan-5-yl-1,1-dimethyl-ethylamino)-propoxy]-phenyl}-propionic acid a) 5-(2-Methyl-propenyl)-indan In a flamed dried flask under argon isopropyltriphenylphosphonium iodide (6.48 g, 15 mmol) in 30 mL of dry THF was cooled to 0° C. Then n-BuLi (2.5 M) in hexanes (6.0 mL) was added via syringe. The reaction mixture was stirred 0° C. for 45 min. Then a solution of the 2,3-dihydro-1H-indene-5-carboxaldehyde (J. Med. Chem. 1993, 36, 3700–3706) was added (1.7, 12.0 mmol) in THF (20 mL) was added drop-wise and the reaction was stirred under Argon at RT overnight. The reaction was filtered, the filtrate was concentrated in vacuo and the residue purified by flash colum chromatography (ethyl acetate/hexane, 1:99) to yield the above titled compound as a pale yellow oil (1.7 g, 67%).

b) N-(2-Indan-5-yl-1,1-dimethyl-ethyl)-acetamide

Following the procedure described in Example 1(c) the above titled compound was obtained as a crystalline solid. Melting point 130–131° C. (ethyl acetate); MS(ES) m/z 463.7 (2M+H)$^+$, 322.7 (M+H)$^+$; Elemental Analysis: theoretical for $C_{15}H_{21}NO$: C, 77.85; H, 915; N, 6.05. found: C, 77.54; H, 9.09; N, 6.03.

c) 2-Inda-5-yl-1,1-dimethyl-ethylamine

Following the procedure described in experiment 1(d), the above titled compound was obtained. MS(ES) m/z 190.6 (M+H)$^+$.

d) Ethyl 3-{4-Cyano-3-[(R)-2-hydroxy-3-(2-indan-5-yl-1,1-dimethyl-ethylamino)-propoxy]-phenyl}-propionate hydrochloride salt.

Following the procedure described in Example 3 using the amine from Example 23(c) the above titled compound was obtained. MS(ES) m/z 465.8 (M+H)$^+$; Elemental analysis: theoretical for $C_{28}H_{36}N_2O_4 \cdot HCl \cdot 3/4H_2O$: C, 65.34; H, 7.44; N, 5.44. found: C, 65.11; H, 7.66; N, 5.25.

e) 3-{4-Cyano-3-[(R)-2-hydroxy-3-(2-indan-5-yl-1,1-dimethyl-ethylamino)-propoxy]-phenyl}-propionic acid Following the procedure described in Example 4 the title compound was obtained. MS(ES) m/z 437.8 (M+H)$^+$.

Example 24

Parenteral Formulation

A pharmaceutical composition for parenteral administration is prepared by dissolving an appropriate amount of a compound of Formula (I) in polyethylene glycol with heating. This solution is then diluted with water for injections (to 100 mL). The solution is then rendered sterile by filtration through a. 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound selected from the group consisting of:
   3-{4-Cyano-3-[(R)-2-hydroxy-3-(2-indan-2-yl-1,1-dimethyl-ethylamino)-propoxy]-phenyl}-propionic ethyl ester;
   3-{4-Cyano-3-[(R)-2-hydroxy-3-(2-indan-2-yl-1,1-dimethyl-ethylamino)-propoxy]-phenyl}-propionic acid;
   3-{4-Cyano-3-[(R)-2-hydroxy-3-(2-indan-2-yl-1,1-dimethyl-ethylamino)-propoxy]-phenyl}-propionic acid isopropyl ester;
   3-{4-Cyano-3-[(R)-2-hydroxy-3-(2-indan-2-yl-1,1-dimethyl-ethylamino)-propoxy]-phenyl}-propionic acid 2-ethoxy ethyl ester;
   3{4-cyano-3-[(R)-2-hydroxy-3-(2-indan-2-yl-dimethyl-ethylamino)-propoxy]-phenyl}-propionic acid 2-methoxy-1-methyl-ethyl ester;
   3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid;
   3-(4-Cyano-3-{(R)-3-[1,1-dimethyl-2-(5,6,7,8-tetrahydro-naphthalen-2-yl)-ethylamino]-2-hydroxy-propoxy}-phenyl)-propionic acid ethyl ester;
   3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid;
   3-(3-Cyano-4-{(R)-3-[1,1-dimethyl-2-(5,6,7,8-tetrahydro-naphthalen-2-yl)-ethylamino]-2-hydroxy-propoxy}-phenyl)-propionic acid ethyl ester;
   3-{4-Cyano-3-[(R)-2-hydroxy-3-(2-indan-5-yl-1,1-dimethyl-ethylamino)-propoxy]-phenyl}-propionic acid ; and
   3-{4-Cyano-3-[(R)-2-hydroxy-3-(2-indan-5-yl-1,1-dimethyl-ethylamino)-propoxy]-phenyl}-propionate ethyl ester; and pharmaceutically acceptable salts and complexes thereof.

2. A compound according to claim 1 selected from the group consisting of:
   3-{4-Cyano-3-[(R)-2-hydroxy-3-(2-indan-2-yl-1,1-dimethyl-ethylamino)-propoxy]-phenyl}-propionic ethyl ester; and
   3-{4-Cyano-3-[(R)-2-hydroxy-3-(2-indan-2-yl-1,1-dimethyl-ethylamino)-propoxy]-phenyl}-propionic acid;
   and pharmaceutically acceptable salts and complexes thereof.

3. A method of treating a bone or mineral disease or disorder selected from the group consisting of fracture healing, osteoarthritis, rheumatoid arthritis, and osteoporosis comprising administering a compound according to claim 1.

4. A method according to claim 3 wherein the bone or mineral disease or disorder is osteoporosis.

5. A method according to claim 3 wherein the compound is co-administered with an anti-resorptive agent.

6. A method according to claim 5 wherein the anti-resorptive agent is selected from the group consisting of estrogen, 1,25 (OH)$_2$ vitamin D3, calcitonin, selective estrogen receptor modulators, vitronectin receptor antagonists, V-H+-ATPase inhibitors, src SH$_2$ antagonists, bisphosphonates and cathepsin K inhibitors.

* * * * *